United States Patent [19]

Madsen et al.

[11] Patent Number: 4,850,805
[45] Date of Patent: Jul. 25, 1989

[54] PUMP CONTROL SYSTEM

[75] Inventors: Kay Madsen, Saratoga; Frans Ludding, Cupertino, both of Calif.

[73] Assignee: Critikon, Inc., Tampa, Fla.

[21] Appl. No.: 25,314

[22] Filed: Mar. 13, 1987

[51] Int. Cl.$^4$ .............................................. F04B 49/60
[52] U.S. Cl. ....................................... 417/18; 417/63; 222/63; 604/152; 604/153; 73/718
[58] Field of Search ........................ 604/131, 151–153, 604/118, 121, 246–247; 128/DIG. 1, DIG. 12, DIG. 13, 722, 672, 675; 417/413, 219, 38, 63, 18; 222/63; 73/718

[56] References Cited

U.S. PATENT DOCUMENTS

| | | |
|---|---|---|
| 3,736,930 | 6/1973 | Georgi . |
| 3,831,588 | 8/1974 | Rinder ................................. 604/118 |
| 3,989,913 | 11/1976 | Lundquist et al. . |
| 4,184,510 | 1/1980 | Murry et al. ........................... 604/22 |
| 4,207,871 | 6/1980 | Jenkins . |
| 4,236,880 | 12/1980 | Archibald ........................... 604/153 |
| 4,255,088 | 3/1981 | Newton et al. ........................ 417/1 |
| 4,261,360 | 4/1981 | Perez ........................... 128/DIG. 13 |
| 4,277,266 | 7/1981 | Archibald ................... 128/DIG. 13 |
| 4,322,201 | 3/1982 | Archibald ........................... 604/152 |
| 4,324,259 | 4/1982 | Wright ............................... 128/722 |
| 4,367,435 | 1/1983 | Bailey et al. . |
| 4,373,525 | 2/1983 | Kobayashi .................. 128/DIG. 13 |
| 4,468,222 | 8/1984 | Lundquist ........................... 604/153 |
| 4,526,574 | 7/1985 | Pekkarinen ................. 128/DIG. 13 |
| 4,583,915 | 4/1986 | Montgomery et al. ................ 417/18 |
| 4,718,576 | 1/1988 | Tamura et al. ....................... 604/153 |

Primary Examiner—John D. Yasko
Assistant Examiner—Kathleen A. Daley
Attorney, Agent, or Firm—W. Brinton Yorks, Jr.

[57] ABSTRACT

A pump control system is described in which the pumping mechanism causes corresponding movement of a pair of capacitor plates. The plates are energized by an a.c. signal, and the signal produced by the plates is amplitude detected, with the amplitude modulation representing pumping force. The pumping force is converted to pumping pressure. The pumping pressure peak during pumping and the pressure minimum during filling are detected to determine the portion of a pumping cycle required to make the transition between these two pressure levels. The difference between the two pressure levels divided by the transition portion of the pumping cycle gives a measure of the compliance of the pump chamber. The ratio of the compliance measure to the total cycle, when multiplied by the nominal chamber volume, gives a measure of unpumped volume, which is subtracted from the nominal volume to give the volume actually pumped during a pump cycle. The volume pumped is compared with a desired flow rate to determine a speed control value for the motor of the pumping mechanism. A motor control signal is developed by subtracting from a constant number a value which is a factor of the spaced control value and the position of the motor.

16 Claims, 7 Drawing Sheets

PUMP CONTROL SYSTEM

This invention relates to fluid delivery systems and, in particular, to control techniques for controlling the delivery of parenteral solutions by intravenous pumps.

Pumping systems for the delivery of fluids intravenously or intra arterially are well known in the prior art and are in widespread daily use in hospitals throughout the world. These systems are commonly used for the intravenous or intra arterial delivery of such fluids as glucose solutions and blood plasma, and for the delivery of drugs, all at controlled delivery rates based on the patient's need, and in the case of drugs, the drug concentration being delivered.

Concurrently filed U.S. Pat. application Ser. No. 025,300, entitled PUMP PRESSURE SENSOR describes a novel pump-pressure sensor combination in which a motor driven flexible beam alternately compresses and expands a disposable pump cassette. The movement of the flexible beam causes relative movement of capacitor plates attached to the flexible beam and to a companion sensor beam. By measuring changes in the capacitance of the capacitor plates, a measure of the pumping force and hence the solution pumped through the cassette may be obtained. Such a system is desirable for users, because the use of a disposable cassette insures that a new, sterile cassette may be used for each infusion procedure. The system is economical since the cassette is produced from inexpensive polymeric materials.

However, the use of a plastic cassette presents difficulties in obtaining fluid measurement accuracy. When pumping forces are applied to the cassette the plastic material will distort, or expand, and the volume of the cassette will change. Such a phenomenon is termed cassette compliance. Correspondingly, when the pumping forces are withdrawn and a negative pressure relative to inlet pressure is produced within the cassette during filling, the plastic cassette will relax to a different volume, which is termed depliance. The varying compliance and depliance of the cassette will lead to errors in the fluid delivery rate.

In accordance with the principles of the present invention, a technique for determining cassette compliance or depliance is provided. The measured cassette compliance or depliance is used to determine the actual volume of fluid which was pumped during a pumping cycle, and this actual volume is then used to calibrate the pumping rate for precisely controlled fluid delivery.

The accuracy of the depliance or compliance measurement is premised upon accurately knowing the fluid pressures within the cassette during the pumping cycle. This, in turn, requires precision in the sensing of pumping forces which are measured by the beam capacitor plates. In accordance with another aspect of the present invention, the plate capacitance is measured by energizing the plates with an a.c. signal. The detected a.c. signal varies in amplitude as the capacitance changes. The a.c. signal is amplitude detected to provide a signal representative of pumping force. This signal is then used to produce a digital signal which quantitatively specifies the pumping force.

Once the desired pumping rate has been calibrated for the effects of cassette compliance, the pump must be controlled to effect the desired fluid delivery rate. In accordance with a further aspect of the present invention, the pump motor is precisely controlled by a feedback loop. In the loop, the motor is driven by a signal which is proportional to a loop error factor. The loop error factor is in part determined by a first predetermined number. As the motor turns, its position is monitored by a position sensor. A position signal from the sensor is used in combination with a pump speed control signal derived from the desired fluid delivery rate to develop a control number. The control number is subtracted from the first predetermined number to produce the loop error factor. This control technique affords particularly precise control at low fluid delivery rates where precision is especially important. In the drawings:

FIGS. 6 and 7 are flowcharts illustrating the determination of pump speed control numbers in the motor controller of FIGS. 5 and 5a.

Figure 1:
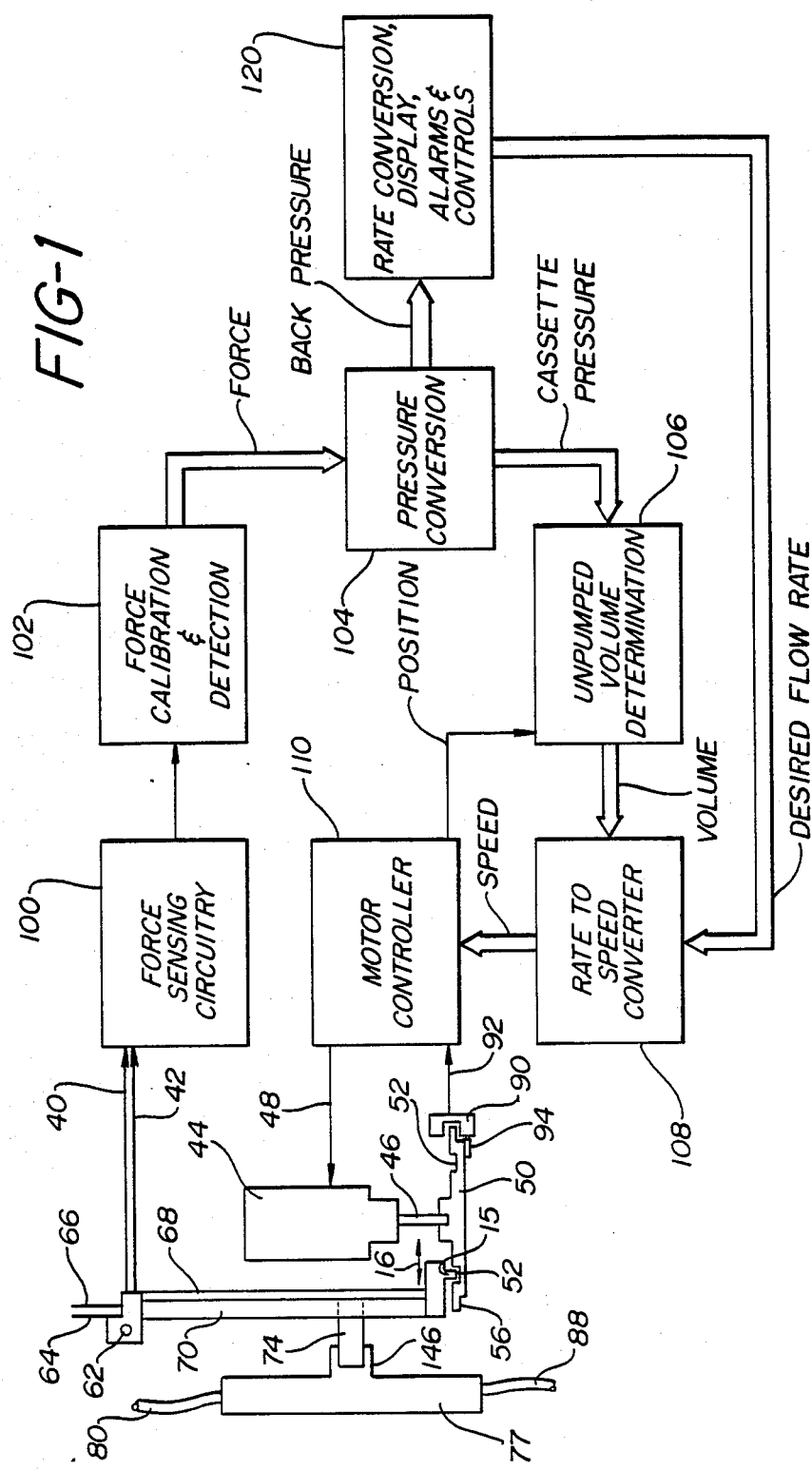
FIG. 1 illustrates, partially in block diagram form and partially in schematic form, a pump control system constructed in accordance with the principles of the present invention.

Referring to FIG. 1, a pump control system constructed in accordance with the principles of the present invention is shown. The control system controls the operation of a motor-driven pump and pump cassette system which are described in further detail in the aforementioned U.S. Pat. application Ser. No. 025,300, the contents of which are incorporated herein by reference. As shown in FIG. 1, the system of that application includes a D.C. motor 44, which is energized to rotate a motor shaft 46. Connected to the shaft 46 is a drive wheel 50, which contains a cam groove 52. The outer periphery of the drive wheel is serrated to form evenly spaced notches and teeth 56 around the perimeter of the wheel. As the drive wheel turns, the teeth 56 pass through an optical position encoder 90. The teeth on the wheel interrupt two light beams directed at the teeth 56 and the intervening notches. The light beams are spaced apart by one quarter of the distance across a notch and tooth, and the light beams are received by two light sensor. As the light beams are interrupted by the teeth the sensors produce two square waves which are in relative quadrature. In a constructed embodiment there are thirty-two teeth around the circumference of the wheel, and the quadrature signals thereby provide position resolution of 1/128th of a wheel revolution.

Located along the edge of the drive wheel 50 is a magnet 94. As the magnet passes by the position encoder 90, it closes a magnetic reed switch in the encoder. The closure of the reed switch informs the system that the pumping cycle has reached a "home", or reference position.

Riding in the cam groove 52 is a cam 15. The cam follows the groove as its radial distance from the shaft 46 varies during the pumping cycle. This variation causes the cam and the beams to which it is attached to move laterally, as indicated by arrow 16. The cam groove and cam thus convert the rotation of the motor shaft to a linearly reciprocating motion.

As the cam reciprocates it moves the bottom of a sensor beam 70 and a flexible beam 68 to which it is attached. The flexible beam 68 is pinned at the top by a pivot pin 62, and as its bottom moves the beam flexes about this pin. The sensor beam remains unflexed during pump operation. Located on the flexible beam intermediate the pivot pin and the drive bearing is a laterally extending pump actuator 74. The pump actuator is barbed so as to be self-threading when it engages the drive receptor 146 of the pump cassette 77. The drive receptor 146 is located on the outer surface of a diaphragm of the pump cassette. The drive receptor and diaghragm are made of a polymeric material such as polyethylene so that the receptor 146 will easily thread onto the barbed pump actuator, and so that the diaphragm will be easily displaced into and out of a fluid chamber within the cassette when driven by the actuator. As the diaphragm is driven into the fluid chamber by the actuator the pressure within the chamber increases until it forces open an outlet valve at the bottom of the cassette. Fluid is then pumped out through an outlet tube 88. As the actuator retracts the diaphragm the outlet valve closes and the decreasing chamber pressure will open an inlet valve at the top of the cassette, allowing the chamber to be filled by fluid supplied by inlet tube 80. The complete cycle of the pump thus consists of a filling operation and a pumping operation.

Located at the top of the flexible beam 68 is a capacitor plate 64, and at the top of the sensor beam is a capacitor plate 66. As the flexible beam flexes during the pump cycle the two capacitor plates will move relative to each other. Their capacitance will vary correspondingly, thereby providing a measure of the force exerted on the cassette diaphragm by the pump actuator 74. This force can be either positive or negative, and is related to the fluid pressure within the chamber of the pump cassette.

The capacitor plates 64 and 66 are connected by leads 40 and 42 to force sensing circuitry 100. This circuitry energizes and decodes signals from the capacitor plates 64 and 66 to provide a signal representative of the pump actuator force on the cassette 77. This signal is applied to force calibration and detection circuitry 102, which produces a quantitative force measurement. The force measurement is used by pressure conversion routines 104 which develop a signal representative of fluid pressure within the cassette and a signal representative of cassette outlet back pressure. A rate conversion, display, alarms and controls subsystem 120 provides a visual indication of various operating parameters in the system, monitors the system for fault conditions, and provides a user interface for entry of system operating parameters. In particular, subsystem 120 provides a means for operator entry of desired flow rate, which is used by the motor controller to establish a rate of pump operation.

The cassette pressure measurement is applied to an unpumped volume determination subsystem 106, together with position signals from a motor controller 110 to enable a determination of the percentage of the cassette's fluid volume which is not being pumped by reason of cassette compliance or depliance. A measure of the fluid volume actually being pumped is provided to a rate to speed converter 108, which produces a signal for the control of pump motor speed. The speed control signal is applied to a motor controller 110 which performs closed loop control of the pump motor 44. Motor energization signals are applied to the D.C. motor by a lead 48, and position signals are returned on leads 92 to close the motor control loop.

Figure 2:
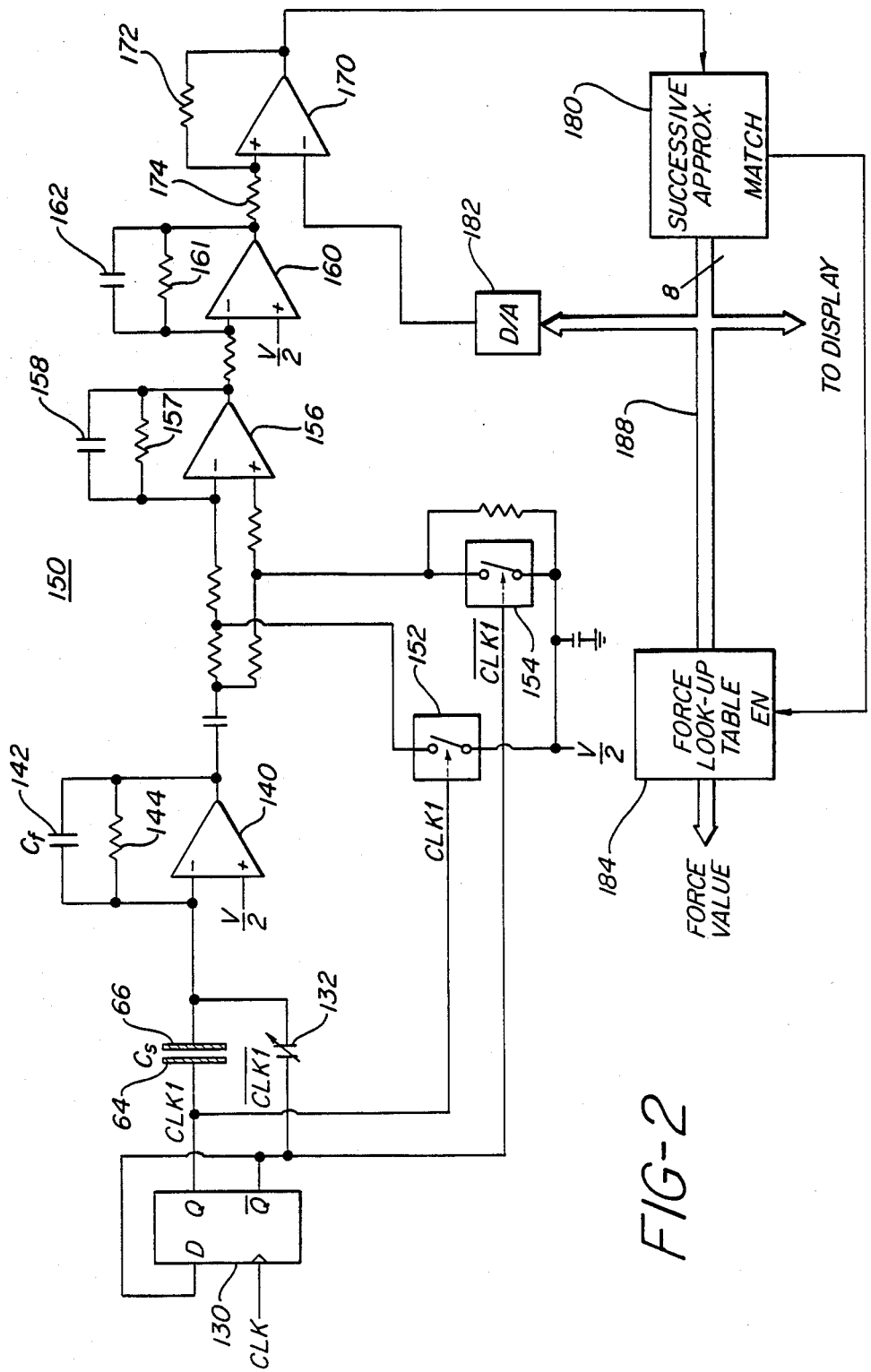
FIG. 2 illustrates, partially in block diagram form and partially in schematic form, details of the force sensing circuitry and the force calibration and detection arrangement of FIG. 1.

Referring to FIG. 2, the force sensing circuitry 100 and the force calibration and detection circuitry 102 are shown in detail. A clock signal CLK of, for instance, 100 kHz is applied to the clocking input of a "D" type flip-flop 130. The $\overline{Q}$ output of flip-flop 130 is coupled to the D input of the flip-flop so that the flip-flop will continually divide the CLK signal by two. Flip-flop 130 produces a $\overline{CLK1}$ signal which is applied to one of the capacitor plates and to the control input of a switch 152. A complementary $\overline{CLK1}$ signal is applied to the trimming capacitor 132 and the CLK1 signal is also applied to the control input of a switch 154. The trimming capacitor 132 is adjusted to null out the stray capacitances in the system. The capacitor plates 64, 66 produce a capacitance $C_s$ which varies with the spacing of the plates, typically over a range of about 1 pf. The changing capacitance of the plates is reflected by an amplitude modulation of the applied a.c. CLK1 signal at the output of an amplifier 140.

The modulated capacitance signal is applied to one input of an amplifier 140. The amplifier 140 has a feedback resistor 144 and a feedback capacitor 142. The gain of this amplifying stage for applied a.c. signals is equal to $C_s/C_f$, where $C_f$ is the capacitance of capacitor 142. A second input of amplifier 140 receives a reference voltage V/2. The circuitry of FIG. 2 is designed to be energized by a conventional +5V. D.C. power supply. This supply voltage is applied to a voltage divider (not shown), which produces a low impedance intermediate voltage V/2. By referencing the capacitance detection circuit to this intermediate voltage level, the a.c. capacitance signal is effectively referenced about this voltage level intermediate the two supply rails. The nominal signal level at the output of amplifier 140 is approximately 50 mv peak to peak.

The a.c. signal at the output of amplifier 140 is capacitively coupled to two inputs of a synchronous detector 150, which synchronously detects the amplitude modulation of the capacitance signal. Also coupled to the inputs of synchronous detector amplifier 156 are the outputs of two synchronously controlled switches 152 and 154. Since the switches are switched by the same CLK1 and $\overline{CLK1}$ waveforms that energize the capacitor plates 64 and 66, the switching is constantly in a known phase relationship with the capacitance signal. These switches alternately operate amplifier 156 to have a high negative gain or a high positive gain, in synchronisum with the a.c. capacitance signal. The synchronous detector 150 thus produces a D.C. level representative of the capacitance of the capacitor plates 64, 66, and hence representative of actuator force. In the illustrated embodiment, the synchronous detector has a gain of about twenty. The "spikes" that occur at the switching of the signals applied to amplifier 156 are filtered by capacitors 158 and 162.

The D.C. signal produced by the synchronous detector 150 undergoes further amplification by an amplifier 160 to produce a final D.C. signal at the output of amplifier 160 which is representative of actuator force at the cassette. The force signal is thereafter detected and calibrated to provide a quantified digital measure of force.

The force representative D.C. signal is applied to the noninverting input of a comparator 170, which compares the level of this signal with the level of a signal produced by a digital to analog (D/A) converter 182. The hysteresis of the comparator is determined by the relative values of resistors 172 and 174 to provide the comparator 120 with hysteresis so that it will change states positively without toggling. The comparison signal produced by the comparator will exhibit one of two states, and indicates whether the force representative signal is greater than or less than the computer generated signal produced by the D/A converter.

The state of the comparison signal is sensed by a successive approximation subsystem 180 which through computer control attempts to match the force representative signal with an eight-bit digital signal on bus 188. The subsystem 180 does this by successive approximation by starting with the most significant bit and setting the bits in sequence on bus 188 in correspondence with sensed changes in state of the comparison signal. The successively updated signal on bus 188 is repetitively converted to an analog signal and compared with the force representative signal until all eight bits have been determined. After eight iterations the digital signal on bus 188 matches the force representative signal to within one part in 256. This iterative technique eliminates the need for a discrete analog to digital converter (A/D) at the output of the amplifier 60.

Once the eight-bit force signal on bus 188 has been determined, it is applied to a force look-up table 184, which produces a corresponding digital signal that is a quantification of actuator force. This may be done in hardware as shown in FIG. 2 by enabling the force look-up table when a match is determined. But it may also easily be done in software. Since eight iterations of the successive approximation comparison will always result in a match, the system will wait until eight successive approximation iterations have been performed before accepting a value from the force look-up table 184. At that time the table will be providing an accurate force value.

During manufacture and calibration of the arrangement of FIG. 1, the force look-up table may be computed from empirical force settings. The cassette 77 is replaced with means for successively applying twelve known forces to the pump actuator 74. These forces may be distributed over a range of +7.5 lbs. to −3 lbs., for instance. After each force is applied, the digital value on bus 188 is displayed and recorded. When all twelve values are recorded they are entered into a curve-fitting routine, which fits a curve of 256 discrete force values to the twelve measurements. The 256 force values are then entered into a read-only memory which serves as the force look-up table for the system.

After a force value has been accepted from the force look-up table 184, the pressure conversion routines (FIG. 1) convert the measured force to several pressure levels that the system needs to know. For instance, the fluid pressure within the cassette in pounds per square inch (p.s.i.) may be found by dividing the force value by the equivalent area of the cassette fluid chamber. The fluid chamber area is easily determined empirically by applying a known force to the cassette and measuring the resultant chamber pressure in p.s.i. The combination of force in pounds and resultant pressure in p.s.i. yields the equivalent area in square inches. For example, if the cassette is found to have an area of 0.5 square inches and the force value is 6.25 pounds, the cassette pressure is the quotient of the two, or 12.5 p.s.i. To determine the fluid pressure at the infusion site, or back pressure, the pressure required to open the cassette outlet valve, or the cracking pressure, is then subtracted from the cassette pressure. If the outlet cracking pressure was 5 p.s.i., for instance, a cassette pressure of 12.5 p.s.i. would yield a back pressure measurement of 7.5 p.s.i. This back pressure measurement is continuously monitored by subsystem 120 to see that it remains within an acceptable range.

Other factors impacting on the measured force may also be taken into consideration in the determination of pressures. For example, the pump actuator or the drive wheel may be spring-loaded to remove backlash from the mechanical components of the system, and the spring force may affect the detected actuator force and have to be factored into the force calculation. In the use of a plastic cassette, the cassette may exhibit forces of resilience, which are a function of the pump operating cycle and pump speed. Also, a plastic cassette may be expected to exhibit some stress relaxation with time of the plastic material of the cassette as a function of the pump operating cycle. All of these factors would be taken into consideration in the conversion of force to pressure measurements.

Figure 3:
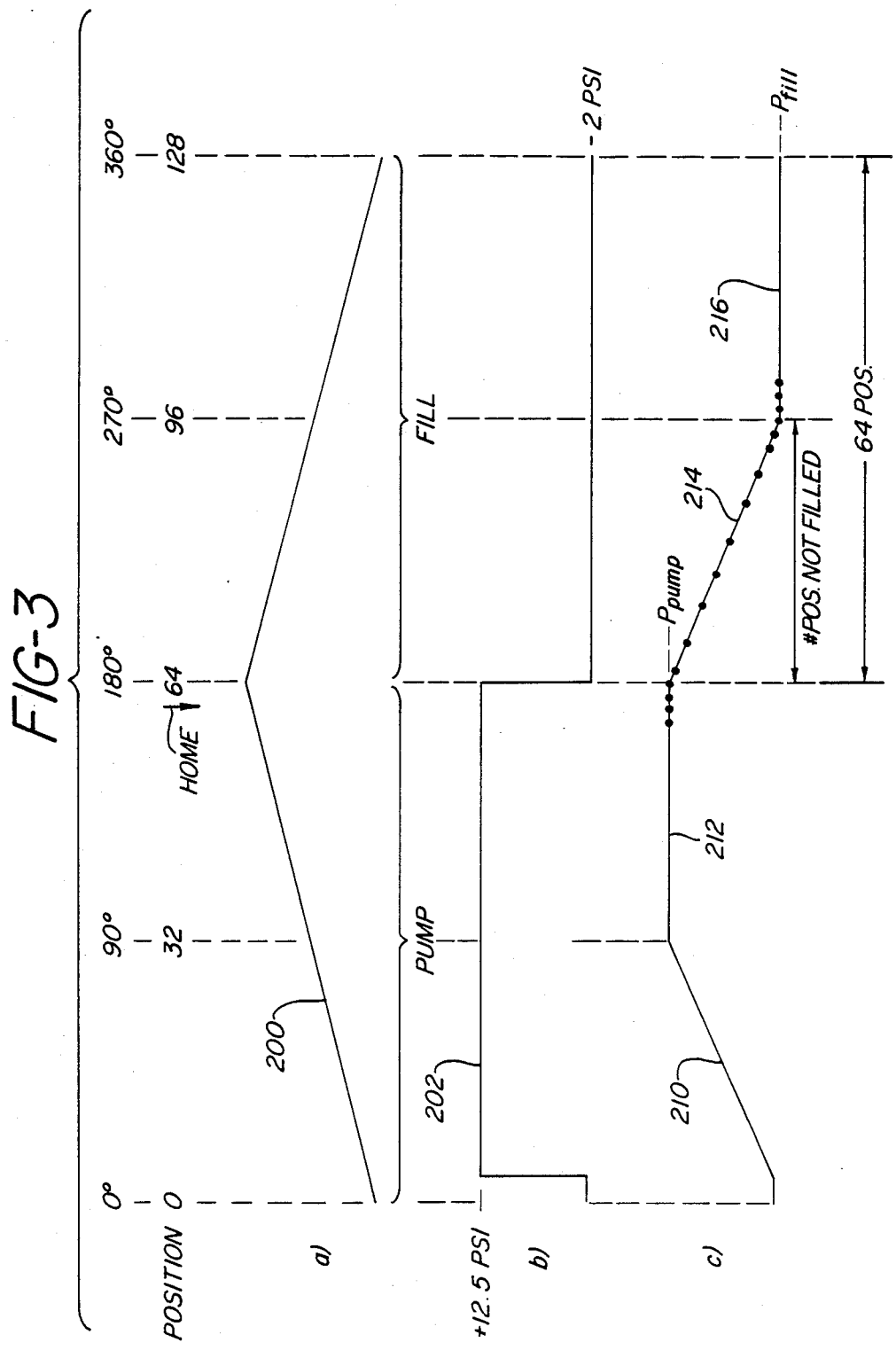
FIG. 3 illustrates waveforms depicting principles of the unpumped volume determination technique of the present invention.

The cassette pressure measurements are used to determine the actual volume of liquid that is pumped by the pump cassette during each pumping cycle. FIG. 3 illustrates the principles of the determination of the volume pumped by the cassette. Curve 200 in FIG. 3a represents the cam height, or variation of cam groove 52 from the drive shaft 46, over one pumping cycle. The pumping cycle is separated into its two phases of operation, the pumping operation when liquid is being expelled through the outlet tube 88, and the filling operation when liquid is refilling the cassette through inlet tube 80. At the top of the figure the cam position is shown in degrees of a full cycle, and also in terms of the 128 different phases of the position sensor signal, which indicate cam position. The pumping operation extends from position 0 to position 64, and the filling operation extends from position 64 to position 128 in this example, although the two operations may be proportioned unequally if desired.

Curve 202 of FIG. 3b shows a typical pressure response for a perfectly noncompliant, e.i., rigid, cassette. In such a cassette, there would be an immediate rise to peak pressure as the pumping operation begins. In the illustration of FIG. 3b, the peak pressure is shown as +12.5 p.s.i. When the cycle shifts from pumping to filling at cam position 64, the cassette pressure falls immediately to its filling pressure, shown here as −2 p.s.i. These pressures will vary from one procedure to another as a function of factors such as back pressure at the outlet of the cassette, and the inlet head pressure determined by the elevation of the fluid source relative to the cassette.

In a polymeric cassette such as cassette 77, the pressure response curve would not be as shown by curve 202, but would exhibit effects of compliance and depliance. A pressure response curve for a cassette which is 50% compliant is shown in FIG. 3c. Due to the 50% compliance, the cassette pressure would rise gradually over the first half of the pumping operation (positions 0 to 32) as shown by line 210. At position 32 the compliance has been absorbed and the pressure levels off at a peak pressure, $P_{pump}$, as the outlet valve opens at its opening (cracking) pressure. The pressure remains as indicated by line 212 until the fill operation begins at position 64. Then the depliance of the cassette affects the pressure, which slowly drops until position 96, as indicated by line 214. Thereafter the fill pressure remains at a level $P_{fill}$ until the filling operation is completed at position 128.

The amount of cassette compliance could be determined by measuring pressure changes during the compliant phase of the pumping cycle, indicated by line 210. However, it is preferred to measure cassette compliance by the effects of dipliance occurring during the filling operation around line 214. The reason for this is that the fluid chamber pressure is independent of distal pressure at that time. Once the filling operation begins, the outlet valve on the cassette closes, thereby isolating the cassette depliance from pressure effects at the infusion site. When the pumping operation is used for compliance determination, the outlet valve is either open or about to open. The pressure level at which the valve actually does open is a function of variables beyond the control of the system, such as the possibility that movement by the patient will suddenly relieve or increase the back pressure at the infusion site. Such movement will not only cause the outlet valve to open at different pressures from one pumping cycle to another; the changing back pressures into the pump cassette can also vary the compliance during the time it is being measured. These difficulties and inaccuracies are avoided by measuring depliance during the filling operation.

Figure 4:
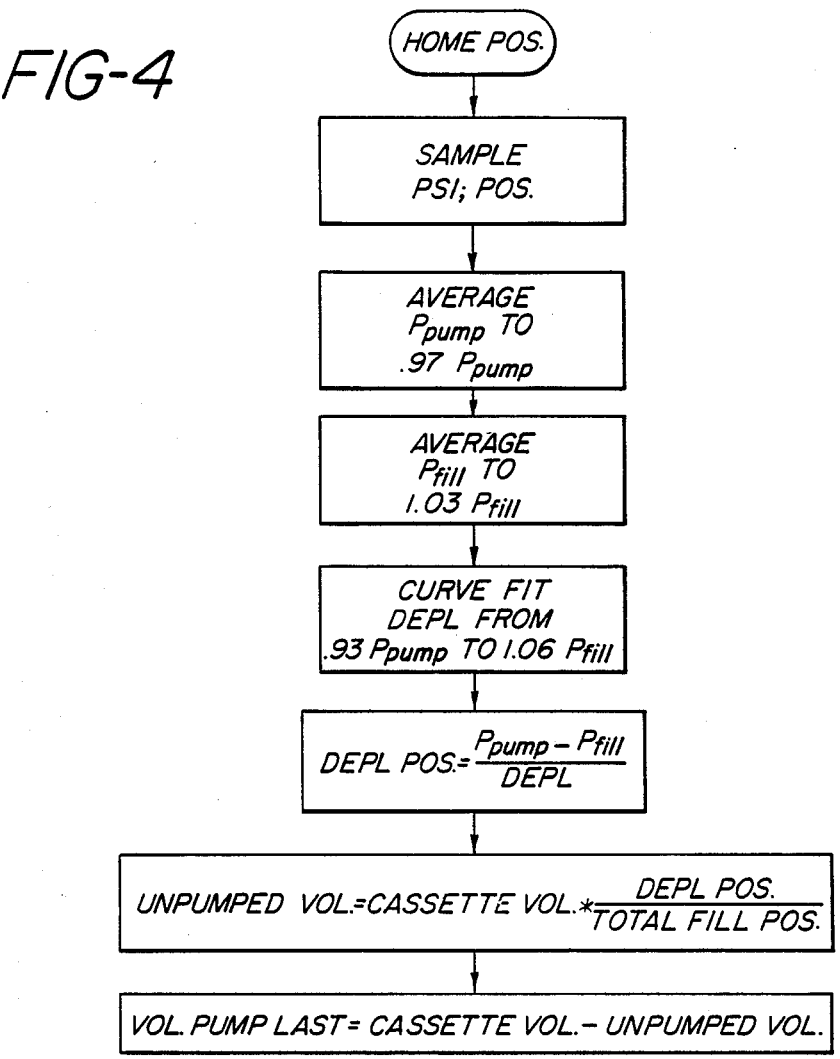
FIG. 4 illustrates a flowchart for making an unpumped volume determination.

Referring concurrently to the flowchart of FIG. 4, the technique for determining the volume of liquid unpumped by reason of cassette compliance and depliance may be understood. The process begins upon receipt of a "home" signal from the position sensor 90. This is the signal produced by closure of the reed switch when the magnet 94 opposes the switch. The home signal informs the system that the cam is approaching position 64 and the filling operation is about to begin. The system then begins to rapidly sample the cassette pressure at corresponding cam positions. Initially these measurements will be at the end of the pumping operation, when the cassette is still pressurized at the $P_{pump}$ pressure, as indicated by the sampling points on line 212. When the filling operation begins, the cassette outlet valve closes and the system continues to acquire data pairs of pressure and position measurements as the effects of depliance occur, as shown by the sampling points on line 214. Finally a stable fill pressure level, $P_{fill}$, is reached, and the system acquires a number of data pairs at this final level.

Next, the system determines the absolute pressure level $P_{pump}$. It does this by accumulating and averaging successive ones of the initial pressure measurements until a measurement is reached which is 97% of the accumulated average. This procedure sets a value for $P_{pump}$. A similar procedure is used to determine the absolute pressure level $P_{fill}$. Later occurring pressure measurements are accumulated and averaged by proceeding backward with respect to the time acquisition until a measurement is reached which is 103% of the accumulated average. This averaging procedure sets the $P_{fill}$ pressure level.

A curve fitting procedure is then used to determine line 214. The data pairs used for the curve fit are those ranging from 106% of the $P_{fill}$ level to 93% of the $P_{pump}$ level. For a cassette exhibiting little depliance there may be only a few of these data points, whereas a highly depliant cassette may yield over a hundred such measurements. The curve DEPL which is fit to these data points will define the depliance curve in terms of the change in cassette pressure with changes in cam position.

The above three measurements are then used to calculate the number of cam positions during which the cassette was undergoing depliance. This calculation is made by dividing the difference between $P_{pump}$ and $P_{fill}$ by the depliance curve DEPL. This calculation determines the number of cam positions when the cassette was undergoing a relaxation of the compliant forces, and was not being filled by reason of this volumetric change. This interval is indicated in FIG. 3 as the "number of positions not filled", and in this example is 32 positions.

The number of cam positions occurring during depliance is then used to determine the unpumped volume. This is the volume of liquid which remains in the cassette during the pumping cycle and occupies the increased fluid chamber volume during compliance. The unpumped volume is determined by dividing the number of depliance positions by the total number of fill positions, then multiplying this ratio by the nominal cassette volume. The cassette volume may be determined empirically by measuring the displacement of the cassette diaphragm when it is extended into the fluid chamber. In a constructed embodiment the cassette volume was measured as 350 µl. For this example, then, the unpumped volume is equal to (350 µl)* (32 pos./64 pos.), or 175 µl.

The volume of liquid actually pumped during the pump cycle is now readily determined by subtracting the unpumped volume from the nominal cassette volume. For the above example, this volume actually pumped in one cycle is 175 µl.

This technique is applicable to any ratio of pumping positions to filling positions which may be employed in a given system. For instance, it may be desirable to rapidly fill the cassette during one-quarter of the pumping cycle, then to pump during the remaining three-quarters of the cycle. Such a pump-fill ratio may be employed to maintain sufficient back pressure at the injection site over most of the pumping cycle to keep a vein open, for instance, and would be desirable at very low infusion rates.

The determination of the volume actually pumped is performed each pumping cycle to accurately measure the infusion rate and to keep an accurate running measurement of the volume of liquid delivered to the patient. While the effects of compliance will generally remain fairly constant during use of a single cassette, compliant variations of up to 20% have been observed from one polymeric cassette to another.

Figure 5A:
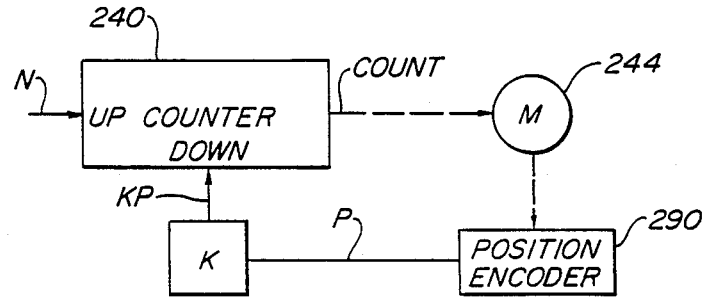
FIG. 5a illustrates in block diagram form the principles of motor control employed in FIG. 5.

The principles of the control loop for motor 44 of FIG. 1 are illustrated in FIG. 5a. In principle, a counter 240 is incremented at an even rate by predetermined pulses N. The output of the counter is an error signal "count" which will in time reach a level which energizes the D.C. motor 244. When the motor is energized its positional change is sensed by position encoder 290, which produces a position signal P. The position signal P is combined with a speed control factor K to produce a product term KP. The term KP decrements the counter 240, thereby reducing the count in feedback control fashion. The control algorithm for motor control may thus be expressed as Count = $N - KP$ This control technique has been found to be especially accurate in its control of a pumping system, particularly at very low rates of infusion. The rate at which the counter 240 is incrementing is always precisely known, since the counter is incrementing at a fixed rate. The rate of infusion is controlled by substracting the term KP from this fixed number N of known rate. At very low rates of infusion the motor will be controlled to turn on and off, and it is desirable to do this without oscillation or abrupt changes in pump motion. By controlling the negative feedback through the KP term, smooth operation is attained. When the Count reaches a level that energizes the motor, a position change is immediately sensed and the counter 240 is decremented by the term KP. At low infusion rates the decrement will reduce the Count below the level of motor energization, turning the motor off by reason of negative feedback. The counter will then increment at an even rate until the motor is again energized, and the control pattern will thus continue in this controlled, repetitive manner.

With this control technique, relatively small K values are used at relatively high rates of infusion, while relatively large K values are employed at very low infusion rates. Such a relationship arises by reason of the fixed rate of the incrementing term N. This relationship provides the use of large values for K at the low infusion rates where high resolution is required for precise control of a low infusion rate.

The term K is expressed in two ways:

$$K = f/\text{rate}, \quad (1) \text{ and}$$

$$K = N_R/V_R \quad (2),$$

where rate is flow rate in ml/hr., $N_R$ is the number of N pulses in one pump cycle (or revolution of the pump motor), $V_R$ is the volume in $\mu$l pumped in one revolution, and f is a conversion factor. The term K is expressed in units of number of N pulses per $\mu$l. Hence, from the first of the two expressions, f is expressed in units of (N pulses)(ml)/($\mu$l)(hr.). Assume now that the fixed rate of N is one pulse (or one up count) every 2.5 msec., or a pulse rate of 400 pulses per second. The conversion factor f can now be determined from a straightforward conversion calculation as 1440 (N pulses) (ml)/($\mu$l)(hr.).

A simple example illustrates the use of these expressions in the implementation of the inventive control technique. In FIG. 1 it is seen that the rate to speed converter receives a desired flow rate from the operator by way of subsystem 120. Assume that the desired flow rate is 100 ml/hr., and that the volume pumped during each revolution of the pump motor is 350 $\mu$l. Expression (1) is now calculated as $$K = 1440/\text{rate} = 1440/100 = 14.4$$

When expression (2) is solved for the number of N pulses in one pump motor revolution, it is seen to be $$N_R = K V_R \quad (3)$$

This expression (3) is seen to be $$N_R = (14.4)(350) = 5040,$$

which is 5040N pulses per pump motor revolution. From FIG. 3 it is seen that there are 128 sensed motor positions in one pump revolution. Dividing 5040 by 128 yields a K value of 39.375. Thus, each time a position signal P is produced, the counter 240 is ideally decremented by 39.375 to run the pumping system at the desired rate of 100 ml/hr.

Over a period of time the Count would stabilize around a given level, while N and KP would be ever increasing. Thus over time $$N \doteq KP$$

where each side of the expression is a multiple of 5040 in this example.

Figure 5:
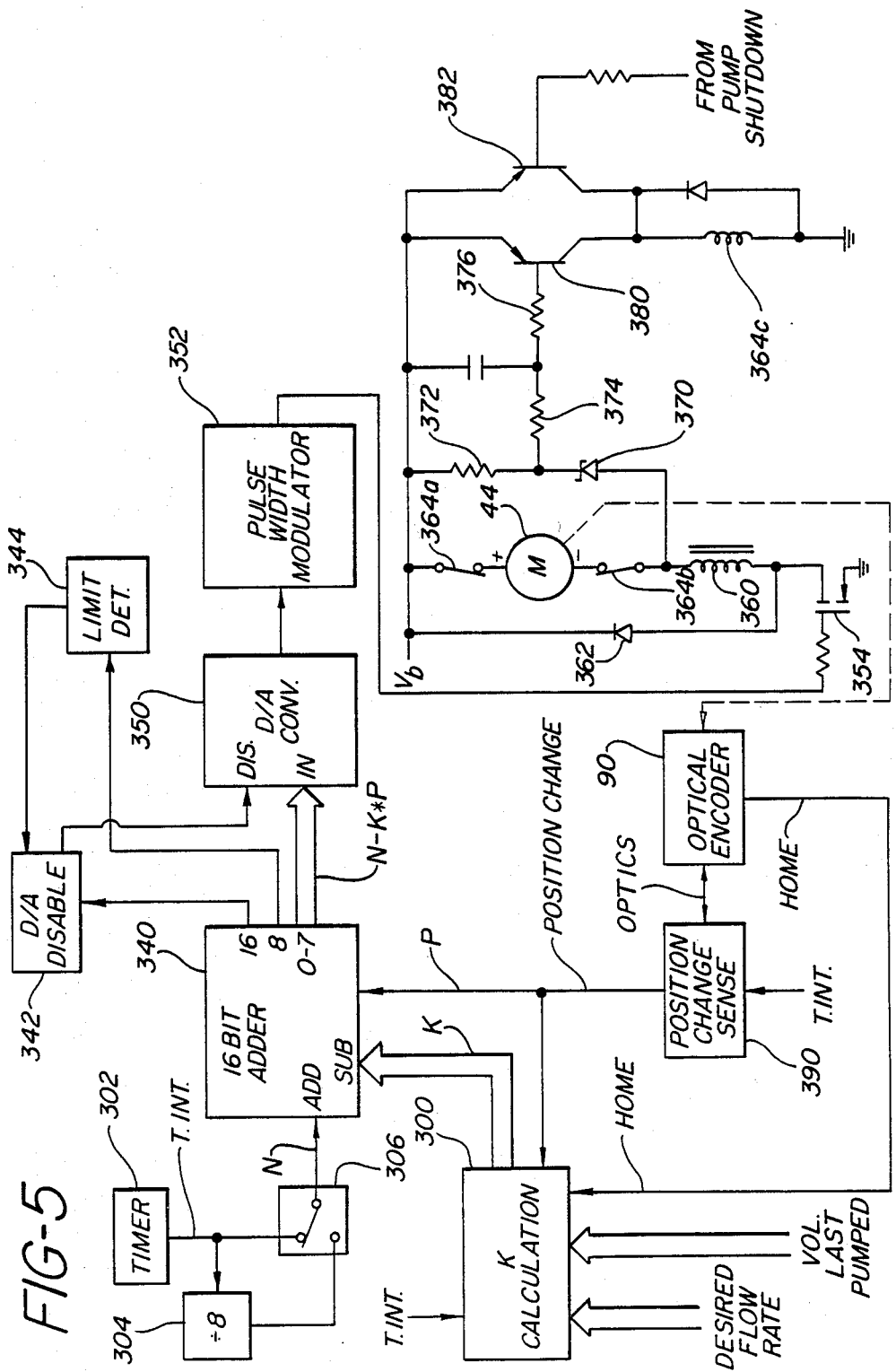
FIG. 5 illustrates, partially in block diagram form and partially in schematic form, details of the motor controller of FIG. 1.
Figure 6:
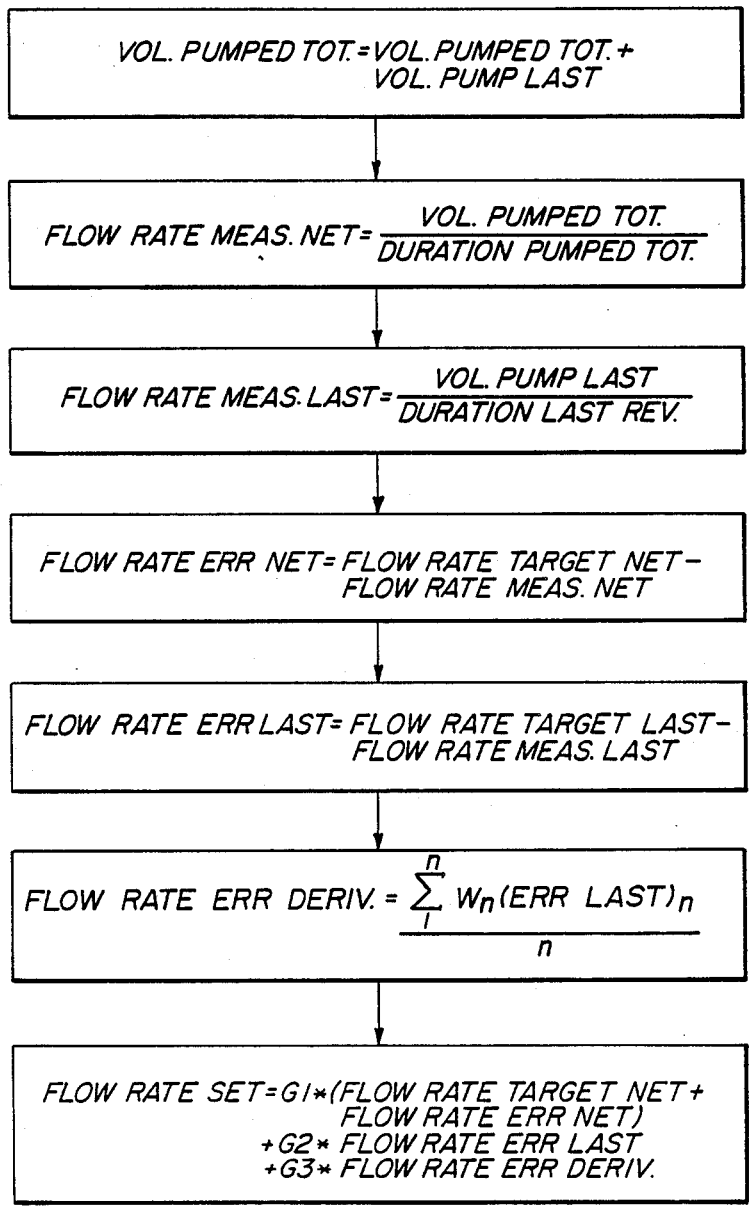
Figure 7:
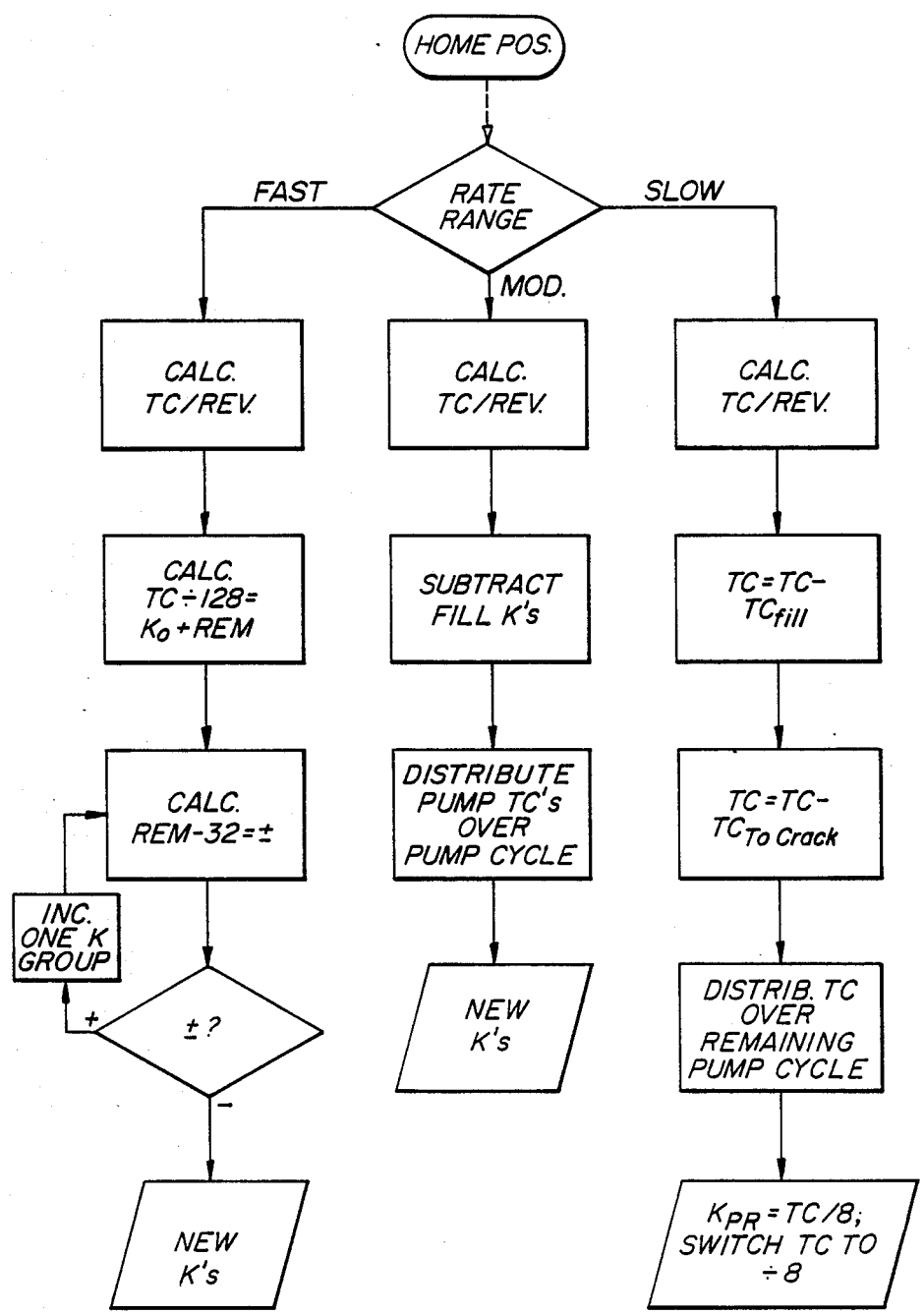

Referring now to FIGS. 5, 6, and 7 the rate to speed converter 108 and the motor controller 110 of FIG. 1 are illustrated in further detail. The calculation of the K value is performed in subsystem 300, which receives the home position signal, the determination of the volume last pumped from the unpumped volume determination subsystem 106 of FIG. 1, and the operator-entered desired flow rate. The subsystem 300 also receives timer interrupts from a 2.5 msec. timer 302. The timer 302 applies timer interrupt pulses to a divide-by-eight counter 304 and to one input of a two-position switch 306. The output of the counter 304 is coupled to a second input of the switch 306. The arm of the switch 306 applies pulses N to an Add input of a 16-bit adder 340. At another input of the adder 340, K values are subtracted whenever a P signal occurs. The lower eight bits (0–7) of the output of the adder 340 are applied to the input of a D/A converter 350. The next most significant bit 8 of the adder output is applied to a limit detector 344, and the sign bit 16 of the adder 340 is applied to a D/A disable subsystem 342. The output of subsystem 342 is coupled to a disable input of D/A converter 350. The output of the limit detector 344 is coupled to an input of the subsystem 342.

The output of the D/A converter 350 is coupled to a pulse width modulator 352, which produces pulses with a width corresponding to the level of the input signal to the modulator. Pulses from the modulator 352 are applied by way of a MOSFET 354 to a coil 360 of the motor circuit. The coil 360 stores and releases energy from the applied pulses to establish a D.C. voltage across the motor 44, which is coupled to a source of supply voltage $V_b$. In series with the motor 144 are shutdown switches 364a and 364b, which are opened when a coil 364c is energized. A diode 362 is coupled across the motor 44 and the coil 360.

The rotation of the shaft of the motor 44 and its drive wheel cause the teeth of the wheel to interrupt the light beams in the optical encoder 90. The encoder's quadrature position signals are applied to a position change sense circuit 390. The home signal is applied to subsystem 300. A position change signal P is provided by the sense circuit 390 to subsystem 300 and the adder 340, as well as the unpumped volume determination subsystem 106 (FIG. 1).

In operation, the total accumulated in adder 340 is incremented continuously by the addition of an N pulse every 2.5 msec when the switch 306 is set as shown in FIG. 5. This is the position of the switch for relatively high flow rates. At very low flow rates the switch is set to its alternate position. The timer interrupt pulses, which occur every 2.5 msec., are then divided by eight, thereby producing an N pulse every 20 msec. The purpose of this scaling will be explained subsequently.

Every time a change in motor position is sensed by circuit 390, a P pulse is produced, causing the adder 340 to subtract the value of K from its accumulated total. Thus the total accumulated in adder 340 is continuously incremented every 2.5 msec or 20 msec by the N pulses, and periodically decremented by an amount K every time a P pulse is produced.

The lower eight bits of the adder 340 are coupled to the D/A converter 350, which converts the count to an analog voltage level. These bits represent the expression $N-K*P$. The D/A converter output level in turn modulates the widths of pulses produced by the pulse width modulator 352 and the pulse width determines the D.C. level applied to motor 44 and hence its speed. In a constructed embodiment, an adder count of about 32 is the threshold at which the motor is energized sufficiently to begin to turn. Counts above 32 cause the motor to turn at proportionately higher speeds. When the adder count reaches 256, bit 8 of the adder changes state, indicating an overspeed condition. This bit is sensed by the limit detector 344 and used by software to turn the pump off. When the adder count first reaches 256, the lower bits 0–7 are initially held at the 255 count to maintain a high motor speed while the system monitors the pump operation to determine if this is just a momentary condition. If it is, the adder will shortly be counted down to a count below 256. But if the count remains above 256 for an unacceptable period of time, the limit detector 344 will trigger the D/A disable subsystem 342, and the D/A converter will be disabled, removing voltage from the motor.

As mentioned previously, when the system is operating at very low flow rates, the values of K are relatively large. The subtraction of these large values from the adder count can expectedly cause a negative number to be accumulated in the adder until the N pulses increment the total back to a positive number. When the adder is retaining a negative number, the adder's sign bit 16 causes the D/A disable subsystem to disable the D/A converter. This prevents the D/A converter from responding to the values of negative numbers as though they were positive, and also conserves battery power in the system while the adder is being incremented back to a positive number.

A fault sensing zener diode 370 and a resistor 372 are coupled across the motor, and resistors 374 and 376 couple and junction of the diode 370 and the resistor 372 to the base of a transistor 380. The coil 364c is coupled between the collectors of transistors 380 and 382 and ground. To guard against motor runaway due to component failures, such as a shorting of the MOSFET 354, the zener diode 370 continuously monitors the motor energization voltage. Excessive motor voltage causes the diode 370 to conduct, which turns on transistor 380. Coil 364c will be energized to open switches 364a and 364b, thereby removing the motor from line currents.

The transistor 382 is responsive to uncontrolled motor operation detected in a pump shutdown system (not shown). In this system, a watchdog timer is normally accessed periodically by the microprocessor of the control system. If the microprocessor senses by the position change signals that the motor is turning without being controlled to do so, the microprocessor will stop accessing the watchdog timer. After a predetermined period without being accessed by the microprocessor, the watchdog timer will cause the pump shutdown system to energize transistor 382 and coil 364c, which will open switches 364a and 364b and remove the motor from line currents.

To conserve battery power, the optical encoder is operated only periodically. On every timer interrupt, one of the light beam emitters in the optical encoder 90 is energized and the output from its corresponding beam sensor is detected and stored. After passage of 2.5 msec, the next timer interrupt causes the sense circuit 390 to energize and sense the other optical signal. The states of the two sensor signals are compared with their previously recorded states. If no change is detected, no output is produced. But if a change in state of one of the signals is detected, the sense circuit 390 produces a P position change pulse at its output. This comparison technique is capable of sensing both positive and negative directions of rotation, and subsystems using the position signal are conditioned to respond accordingly. The number of P pulses occurring since the last home signal, and thus a measure of the current cam position, is accumulated by a P pulse counter in the subsystem 300.

In a preferred embodiment of the present invention, the functions of the K calculation subsystem 300 are efficiently performed by microprocessor software routines, outlined in the flowcharts of FIGS. 6 and 7. Starting at the top of the flowchart of FIG. 6, the total volume of solution that the pump has delivered previously during the infusion procedure (vol. pumped tot.) is updated by adding the volume pumped during the last pump cycle, measured by subsystem 106, to the current accumulation. The measured flow rate (net) over the procedure is then calculated by dividing vol. pumped tot. by the time the pump has been operating (duration pumped tot.). The flow rate measured during the last pump cycle is calculated by dividing vol. pump last by the duration of the last pump revolution. A long term flow rate error (net) is calculated by subtracting flow rate meas. net from the operator's desired flow rate (flow rate target net). A short term flow rate error over the previous pump cycle (flow rate error last) is calculated by subtracting flow rate meas. last from the flow rate target of the last pump revolution. To provide a quick response to a major change in flow rate, a derivative term is calculated by averaging a weighted sum of the last several flow rate errors. A target flow rate for the next pump revolution, flow rate set, is now calculated by weighting and summing flow rate target net and flow rate error net, flow rate error last, and flow rate error derivative. The choice of values for weighting factors G1, G2, and G3 provides a means for selecting the desired response of the system to changes in the various long and short term operating parameters.

The flow rate set calculation, expressed in ml/hr., has been adjusted for cassette compliance, since it starts from the volume actually pumped during the last pump cycle as measured by the compliance measuring subsystem. Thus, the actual number would generally appear to be greater than the desired flow rate set by the operator. If the cassette has a 50% compliance, for instance, the flow rate set for a desired 100 ml/hr. infusion rate could appear as 200 ml/hr. as a result of the compliance correction. It will be appreciated from the foregoing that the flow rate set calculation will continually drive the system to the desired rate of flow.

Once the flow rate set figure has been determined there are several ways to arrive at the appropriate K value for the motor control loop. One direct approach would be to use the flow rate set figure to directly access a look-up table of K values. Each flow rate set figure would access a corresponding K value from the table, or a series of K values to be used at various times during the pumping cycle. For instance, the flow rate set figure could look up two K values, one to be used during the pumping operation and another to be used during the filling operation. More than two K values could be used to speed up, then slow down the pump during the cycle, for instance.

Such a K value look-up table has been formulated, but has been found to use a significant amount of memory. Accordingly, it is preferred to calculate K in accordance with software routines outlined by the flowchart of FIG. 7. New K values are calculated each pumping cycle beginning at a predetermined point in the pumping cycle, such as the occurrence of the home position signal. The program first determines whether the flow rate set number falls within a range of high flow rates (fast), moderate flow rates, or low flow rates (slow). If the number is in a high range, such as 740 ml/hr. in the following example, the program proceeds down the left-hand column of the flowchart.

The first step in each branch of the flowchart is to calculate timer interrupt counts TC per pump revolution. Assume that the compliance measurement determined that 300 μl is actually pumped during each pumping cycle. Using the above expressions (1) and (3), it is seen that $N_R = (1440/740)(300) = 584$ TC/rev.

The next step is to distribute the 584 TC/rev. over the 128 pump positions. Dividing 584 by 128 yields an initial $K_o$ value of four for each position, with a remainder of 72. The 128 pump positions are grouped into four groups of 32 positions, two for the pumping operation and two for the filling operation. The $K_o$ values in this example for each position in the four groups are 4, 4, 4, and 4, respectively.

The remainder of 72 is now distributed in increments of 32 over each group of 32 positions, beginning with the group of the last 32 filling positions. The number 32 is subtracted from the remainder of 72, giving a further remainder of 40. Since the further remainder is positive, the K values for the positions in the last group are incremented to five, and the sequence of the four groups is now 4, 4, 4, 5.

The remainder of 40 is reduced again by 32, again giving a positive remainder, this time equal to 8. The positive remainder requires that another group be incremented, and the sequence of the four groups is now 4, 4, 5, 5.

The remainder of 8 is reduced again by 32, this time giving a negative result. In response to this negative result, the routine exits the loop and the K values for the next cycle are in a group sequence of 4, 4, 5, 5.

This means that, for the first 32 P pulses of the pump cycle, a K value of 4 is employed. The sum of the K values for this quarter cycle is hence 128. The same K value of 4 is used during the second half of the pumping operation, and the total K values during pumping is therefore 256.

Similarly, a K value of 5 is used for the 64 P pulses of the filling operation, giving an accumulation of 320 K values over the filling operation. During both pumping and filling a total of 576 K values are subtracted from the count total of the adder, and during this time 576 N pulses will increment the adder. This is within 1.4% of the desired 584 TC/rev., meaning that the pump will be operating slightly faster than the desired speed. This small error will be adjusted during the recalculation of the flow rate set figure after the new pumping cycle has ended.

To illustrate the middle branch of the flowchart, assume that the flow rate set figure is 85 ml/hr., and that the measured volume pumped in one revolution is 302.2 μl. Again using expressions (1) and (3), it is seen that $N_R = (1440/85)(302.2) = 5120$ TC/rev. At this moderate infusion rate, a predetermined K value is used to maintain the fill rate at an equivalent flow rate of about 175 ml/hr. The predetermined K value for each position during filling is 16, for a total K accumulation of 1024 over the 64 fill positions. The TC/rev. figure of 5120 is reduced by this K accumulation to give a figure of 4096 which must be distributed over the pumping cycle. Dividing 4096 by the 64 pumping positions gives a K value of 64, which is subtracted at each P pulse occurrence during the pumping operation. Thus, for this example, a K of 16 is subtracted from the adder count accumulation at each position during filling, and a K of 64 is subtracted at each position during pumping, for a total K of 5120, equal to the expected number of N pulses. It is seen that these K values for the moderate rate are substantially greater than the values of 4 and 5 used in the higher rate example.

The third, slow rate branch of the flowchart is a modification of the moderate rate procedure. At these very low rates of flow the expected TC/rev. are very sizeable. For instance, a rate of one ml/hr. using a cassette pumping 300 μl per revolution would result in a TC/rev. figure of 432,000. However, in order to maintain a positive back pressure during most of the pumping cycle, the cassette is once again filled at the equivalent rate of 175 ml/hr., requiring a total K value of 1024. The TC/rev. figure is decremented by this amount, $TC_{fill}$. The pumping cycle begins at the same 175 ml/hr. rate and the cassette pressure is monitored until the outlet pressure stabilizes once the outlet cracking pressure is reached and the outlet valve opens. This could, for example, take ten pumping positions, which accumulate 160 K values. This number, termed $TC_{To\ Crack}$, is also subtracted from the TC/rev. figure. After these two operations the pump has been rapidly filled and quickly pumped to establish a positive back pressure at the infusion site.

The decremented TC/rev. figure is still in excess of 430,000, however, and this number is now distributed over the remaining number of positions of the pumping operation, in this example 54, to establish the desired flow rate of one ml/hr.. This yields a very large K of almost 8,000. To scale the system for this large value, the K values are divided by eight which gives a K for the remaining positions of the pumping operation, $K_{PR}$, of approximately 1000. Correspondingly, the switch 306 is switched to divide the timer interrupt pulse train by eight, which scales the number of N pulses.

As an alternative to performing the scaling at the end of the calculations as shown in FIG. 7, it may be preferable to begin the calculation sequence with prescaled numbers. Since the actual pumping of liquid begins only after the outlet cracking pressure has been attained after the first ten pumping positions, liquid is being pumped during only the last 54 of the 64 pumping positions. Hence, the volume pumped during one full pumping cycle, 350 μl in this illustration, must be multiplied by 54/64. This yields a volume per revolution of 295.3 μl. Expressions (1) and (3) are now solved using this value, and using a scaled value of $f/8 = 1440/8 = 180$. Thus, it is seen that $$N_R = (180/1)(295.3) = 53.154 \text{ TC/rev.}$$

The $TC_{fill}$ K value is scaled by eight to yield $1024/8 = 128$, and the $TC_{To\ Crack}$ value is likewise scaled, giving $160/8 = 20$. Subtracting these two values from 53,154 results in a TC/rev. figure of 53,006 to be distributed over the 54 pumping positions that liquid is being delivered. The K value per pumping position is seen to be approximately 982. The scaled values of 2 for each of the 64 fill positions and 2 for each of the ten pumping positions until the outlet valve opens are employed during those phases of the pumping cycle.

It will be appreciated that, at this very low flow rare of one ml/hr., the pump is advancing one position in about twenty seconds. Also, it may be seen that each subtraction of a K value on the order of 1000 will drive the adder count to a substantial negative number, which establishes the start and stop mode of operation of the motor necessary to maintain the very low rate of infusion.

What is claimed is:

1. In a liquid pumping system, including a pump chamber which may exhibit compliance and which is operable in a filling cycle and in a pumping cycle, apparatus comprising:
   means for measuring the pressure within said chamber during filling and during pumping; and
   means for determining the portion of a cycle over which the pressure within said chamber is undergoing a transition between a substantially constant pumping pressure and a substantially constant filling pressure;
   wherein the ratio of said portion to said total cycle indicates the compliance of said chamber.

2. The system of claim 1, further comprising:
   means for determining the ratio of said portion to said total cycle; and
   means for calculating the product of said ratio and the nominal volume of said chamber to determine the volume of liquid not pumped by reason of compliance.

3. The system of claim 2, further comprising:
   means for subtracting said volume of liquid not pumped by reason of compliance from said nominal volume of said chamber to determine the volume of liquid pumped by said system.

4. The system of claim 1, wherein said portion of a cycle is a portion of said filling cycle, and wherein said total cycle is the total filling cycle.

5. A method for measuring the compliance of a liquid pumping chamber in which for displacing liquid is moved into and out of said chamber in alternating pumping and filling cycles comprising the steps of:
   (a) measuring a substantially constant pumping pressure level;
   (b) measuring a substantially constant filling pressure level;
   (c) measuring the change in displacement of said displacing means as the pressure undergoes a transition between said pumping and filling pressure levels; and
   (d) dividing the difference between said pumping and filling pressure levels by said change in displacement to obtain a measure of compliance.

6. The method of claim 5, further comprising the step of:
   (e) dividing said measure of compliance by the total displacement change of said displacing means during the cycle in which said change in displacement was measured to obtain a compliance ratio.

7. The method of claim 6, further comprising the step of:
   (f) multiplying said compliance ratio by the nominal volume of said chamber to determine the volume of liquid not pumped by reason of compliance.

8. The method of claim 13, further comprising the step of:
   (g) subtracting said volume of liquid not pumped by reason of compliance from said nominal volume to determine the volume of liquid pumped.

9. A method of operating a liquid pumping system which includes a pump chamber having an inlet and an outlet, with a valve located at said outlet which opens upon the attainment of a given pressure level within said chamber, said pumping system being operable in a filling operation during which said chamber is filled with liquid, and in a pumping operation during which pressure is applied to the liquid within said chamber, comprising:
   operating said pumping system at a predetermined rate during said filling operation;
   operating said pumping system at a predetermined rate during an initial portion of said pumping operation until said given pressure level is attained; and
   thereafter, during the pumping operation, operating said pumping system at a rate which provides a desired flow of liquid.

10. The method of claim 9, wherein each of said predetermined rates are greater than said rate which provides a desired flow of liquid.

11. The method of claim 10, wherein each of said predetermined rates are equal to each other.

12. In a liquid pumping system, apparatus for controlling the speed of a continuous D.C. pump motor which is energized by a continuous D.C. voltage comprising:
   means for detecting motor movement;
   means for calculating a speed control factor based upon a desired pumping rate;
   a source of signals which recur at a predetermined rate;
   counter means which is incremented in correspondence with said recurring signals, and which is decremented in correspondence with detected motor movement and said speed control factor, to produce a motor control signal; and
   means for energizing said D.C. pump motor with a D.C. voltage in response to said motor control signal.

13. The liquid pumping system of claim 12, wherein said means for detecting motor movement comprises a position sensor.

14. The liquid pumping system of claim 13, wherein said counter means is decremented by an amount K whenever a change in motor position in a given direction is detected.

15. The liquid pumping system of claim 14, wherein said recurring signals are represented by a term N, said changes in motor position are represented by a term P, and said motor control signal is represented by the expression N minus K times P.

16. The liquid pumping system of claim 14, wherein said means for energizing said motor includes a digital to analog converter and a pulse width modulator.

* * * * *